United States Patent [19]

Sifniades et al.

[11] Patent Number: 5,457,197
[45] Date of Patent: Oct. 10, 1995

[54] MONOMER RECOVERY FROM MULTI-COMPONENT MATERIALS

[75] Inventors: Stylianos Sifniades, Madison; Alan B. Levy, Randolph, both of N.J.

[73] Assignee: AlliedSignal Inc., Morristown, N.J.

[21] Appl. No.: 225,273

[22] Filed: Apr. 8, 1994

[51] Int. Cl.⁶ .................................. C07D 201/12
[52] U.S. Cl. .................... 540/540; 562/483; 562/485; 562/487; 562/593; 564/488; 564/498; 568/868
[58] Field of Search ............... 540/540; 562/483, 562/485, 487, 593, 488, 498; 568/868

[56] References Cited

U.S. PATENT DOCUMENTS

| | | | |
|---|---|---|---|
| 3,742,093 | 6/1973 | Skidmore | 260/893 |
| 3,917,507 | 11/1975 | Skidmore | 159/2 |
| 4,051,212 | 9/1977 | Grigat et al. | 264/102 |
| 4,107,160 | 8/1978 | Dicoi et al. | 260/239.3 |
| 4,136,251 | 1/1979 | Bice et al. | 528/486 |
| 4,311,642 | 1/1982 | Crescentini et al. | 260/239.3 |
| 4,605,762 | 8/1986 | Mandoki | 562/483 |
| 5,169,870 | 12/1992 | Corbin et al. | 521/49.8 |
| 5,216,149 | 6/1993 | Evans et al. | 540/538 |

FOREIGN PATENT DOCUMENTS

| | | | |
|---|---|---|---|
| 143502 | 11/1969 | Czechoslovakia | 540/540 |
| 568882 | 11/1963 | European Pat. Off. | 540/540 |

OTHER PUBLICATIONS

Journal of Polymer Science, vol. XXX, (1958), S. Smith, "The Re-equilibration of Polycaproamide", pp. 459–478.

Primary Examiner—Robert T. Bond
Attorney, Agent, or Firm—Melanie L. Brown; John E. Thomas; Roger H. Criss

[57] ABSTRACT

A process for recovering monomer from multi-component waste material that includes a hydrolyzable polymer, the process including contacting the multi-component waste material with water and subjecting the resulting mixture to heat and pressure to form a liquid aqueous portion which mainly includes depolymerization products of the hydrolyzable polymer and a water insoluble portion which mainly includes components other than the depolymerization products; separating the liquid aqueous portion and the water insoluble portion; subjecting the separated aqueous portion to a pressure that is lower than that of step (a) and heat to produce a residue and a distillate which contains monomer; and separating the monomer in the distillate from other components in the distillate. The process is particularly useful for recovering caprolactam from waste materials that include nylon 6.

24 Claims, 2 Drawing Sheets

MONOMER RECOVERY FROM MULTI-COMPONENT MATERIALS

FIELD OF THE INVENTION

The present invention relates to a process for the recovery of monomers from multi-component, hydrolyzable polymeric waste materials, particularly caprolactam from waste materials that include nylon 6.

BACKGROUND OF THE INVENTION

Recovery of caprolactam from nylon 6 scrap (in other words, nylon 6 polymer that is substantially free of non-nylon 6 materials) has been practiced for at least twenty years. In general, nylon 6 is depolymerized by heating at elevated temperatures, usually in the presence of a catalyst and/or steam. The caprolactam produced is removed as a vapor stream. An extensive review of the field has been given by L. A. Dmitrieva et al, Fibre Chemistry, Vol. 17, No. 4, Mar. 1986, pp 229–241. Depolymerization of hydrolyzable polymers that are produced as scrap during the manufacture of fiber, chip, film or molded articles is also described in U.S. Pat. No. 4,605,762 to Mandoki. The process includes introducing the polymeric scrap into a hydrolyzer at a temperature of 200° to 300° C. and a pressure of at least 15 atmospheres, wherein high pressure steam is introduced into the lower portion of the hydrolyzer below the polymeric scrap. An aqueous solution of the products of the hydrolysis reaction is withdrawn from an upper portion of the hydrolyzer.

In the case of multi-component mixtures or composites that contain nylon 6 as one component, however, recovery of caprolactam is complicated by the presence of the other components. These other components and/or their decomposition products generated under conventional nylon 6 depolymerization conditions interfere with the isolation of caprolactam of adequate purity, thus necessitating expensive additional purification steps.

It would be particularly beneficial if an inexpensive method could be developed for the recovery of caprolactam from multi-component composites or materials that include nylon 6, such as carpets. The prospect of recycling such material presents a tremendous opportunity to reduce landfill usage and the costs of disposal, as well as an opportunity to reuse natural resources.

Carpets include a face fiber that is adhered to a backing (support) material which may include jute, polypropylene, latex (such as a styrene-butadiene rubber (SBR)) and a variety of inorganic materials such as calcium carbonate, clay or hydrated alumina fillers. Nylon 6 is often used for the face fiber. Typically, the face fiber constitutes only 20–50% by weight of the carpet, the rest of it consisting of the backing materials. In addition, the fiber contains dyes, soil repellants, stabilizers and other compounds added during fiber and/or carpet manufacture. Waste carpet may also contain a host of other impurities, which will collectively be referred to herein as "dirt".

These non-nylon 6 components interfere with caprolactam recovery. For example, one of the most difficult problems is that alkaline components, such as the calcium carbonate filler, neutralize the acidic catalysts, such as phosphoric acid, that are conventionally used to promote nylon 6 depolymerization, thus requiring the use of increased amounts of catalyst. Another problem is that polypropylene and latex partially decompose to a mixture of hydrocarbons that co-distill with caprolactam. The remaining, partially decomposed, non-distilled portion, along with the filler and other inorganic components, renders the reaction mixture very viscous and difficult to process in conventional equipment.

U.S. Pat. No. 5,216,149 to Evans et al. attempts to solve the general problem of reclaiming useable materials from multi-component plastic waste by using "fast pyrolysis in a carrier gas" in the presence of a catalyst. Example 1 of the patent is directed to the recovery of caprolactam from a waste stream containing nylon 6. The reaction is conducted at a temperature sufficiently high to cause pyrolysis of nylon 6 but not of the other components. However, in the exemplified experiments for which data is reported the only other component used in the waste stream mixture with nylon 6 was polypropylene.

U.S. Pat. No. 5,169,870 to Corbin et al. also describes a method for attempting to reclaim caprolactam from carpets that contain nylon 6 face fibers. The method includes mechanically separating a portion of the non-nylon 6 components and catalytically depolymerizing the resultant enriched nylon 6 fraction in the presence of superheated steam. The crude yield of caprolactam given in Example 1 of the patent was 56%; steam and 85% phosphoric acid were used respectively at the rate of 33 and 0.55 parts per part of crude caprolactam produced. It is stated in the patent that the initial mechanical separation step is not necessarily required and in Example 3 of the patent a carpet was depolymerized without prior mechanical separation and steam and 85% phosphoric acid were used respectively at the rate of 51 and 0.30 parts per part of crude caprolactam produced.

In Czechoslovakian Pat. No. 143,502 to Petru et al. there is described a process for the recovery of caprolactam from a waste material that includes nylon 6 and a non-nylon 6 component, such as in tires, laminated plastic sheets or textiles from mixed fibers. The waste material is heated under pressure in water at the melting point of nylon 6. The extracted nylon 6 is subsequently subjected to a separate step of thermal depolymerization, with or without prior separation from water or another solvent.

Smith, S., in the Journal of Polymer Science, Vol. 30, pp. 459–478 (1958), describes the depolymerization of nylon 6 in the presence of water in a sealed system as being an equilibrium reaction. This article reports both the rate and the equilibrium composition at 230° and 270° C.

A need still exists, however, for an efficient process for recovery of caprolactam from multi-component materials that include nylon 6.

SUMMARY OF THE INVENTION

It is an object of the invention to provide a process for recovering monomer from multi-component, waste materials that include at least one hydrolyzable polymer that avoids the problems associated with the previous recovery methods that have been attempted.

In accomplishing the foregoing object there is provided according to this invention a process for recovering monomer from a multi-component material that includes at least one hydrolyzable polymeric component, comprising:

(a) subjecting a mixture of water and the multi-component material to heat and pressure to form a liquid aqueous solution which includes as a major constituent a mixture of depolymerization products of the hydrolyzable polymeric component and a water insoluble portion which includes as a major constituent a mixture of materials other than the depolymerization products;

(b) separating the liquid aqueous solution and the water insoluble portion;

(c) flashing and heating the liquid aqueous solution to produce a distillate which contains at least one type of monomer from which the hydrolyzable polymeric component was formed and a residue; and (d) separating the monomer in the distillate from other components in the distillate.

The depolymerization of the hydrolyzable polymeric component occurs in steps (a) and (c) and, preferably, does not require a catalyst. Steps (a) and (b) can both be performed continuously in an extruder.

According to a preferred embodiment, there is provided a process for recovering caprolactam from carpet material that includes nylon 6 and non-nylon 6 components, comprising:

(a) subjecting a mixture of water and the carpet material to heat and pressure to form a liquid aqueous solution which includes as a major constituent a mixture of nylon 6 depolymerization products and a water insoluble portion which includes as a major constituent a mixture of non-nylon 6 components;

(b) separating the liquid aqueous portion and the water insoluble portion;

(c) flashing and heating the liquid aqueous portion to produce a residue and a distillate which contains caprolactam; and (d) separating the caprolactam in the distillate from other components in the distillate.

A further embodiment provides a process for recovering caprolactam from a carpet material that includes nylon 6 and non-nylon 6 components, comprising:

(a) introducing the carpet material and water into a first reactor, preferably an extruder;

(b) subjecting the resulting mixture to heat and pressure to form a liquid aqueous portion which includes as a major constituent a mixture of nylon 6 depolymerization products and a water insoluble portion which includes as a major constituent a mixture of non-nylon 6 components;

(c) separating the liquid aqueous solution and the water insoluble portion;

(d) introducing the liquid aqueous solution into a second reactor;

(e) subjecting the liquid aqueous solution to heat and pressure sufficient to produce a residue and a distillate which contains caprolactam; and (f) separating the caprolactam from other components in the distillate produced in step (e).

Further objects, features and advantages of the invention will become apparent from the detailed description of preferred embodiments that follows.

BRIEF DESCRIPTION OF THE DRAWING

The invention will be described in more detail below with reference to drawing, wherein.

DETAILED DESCRIPTION OF THE PREFERRED EMBODIMENTS

Figure 1:
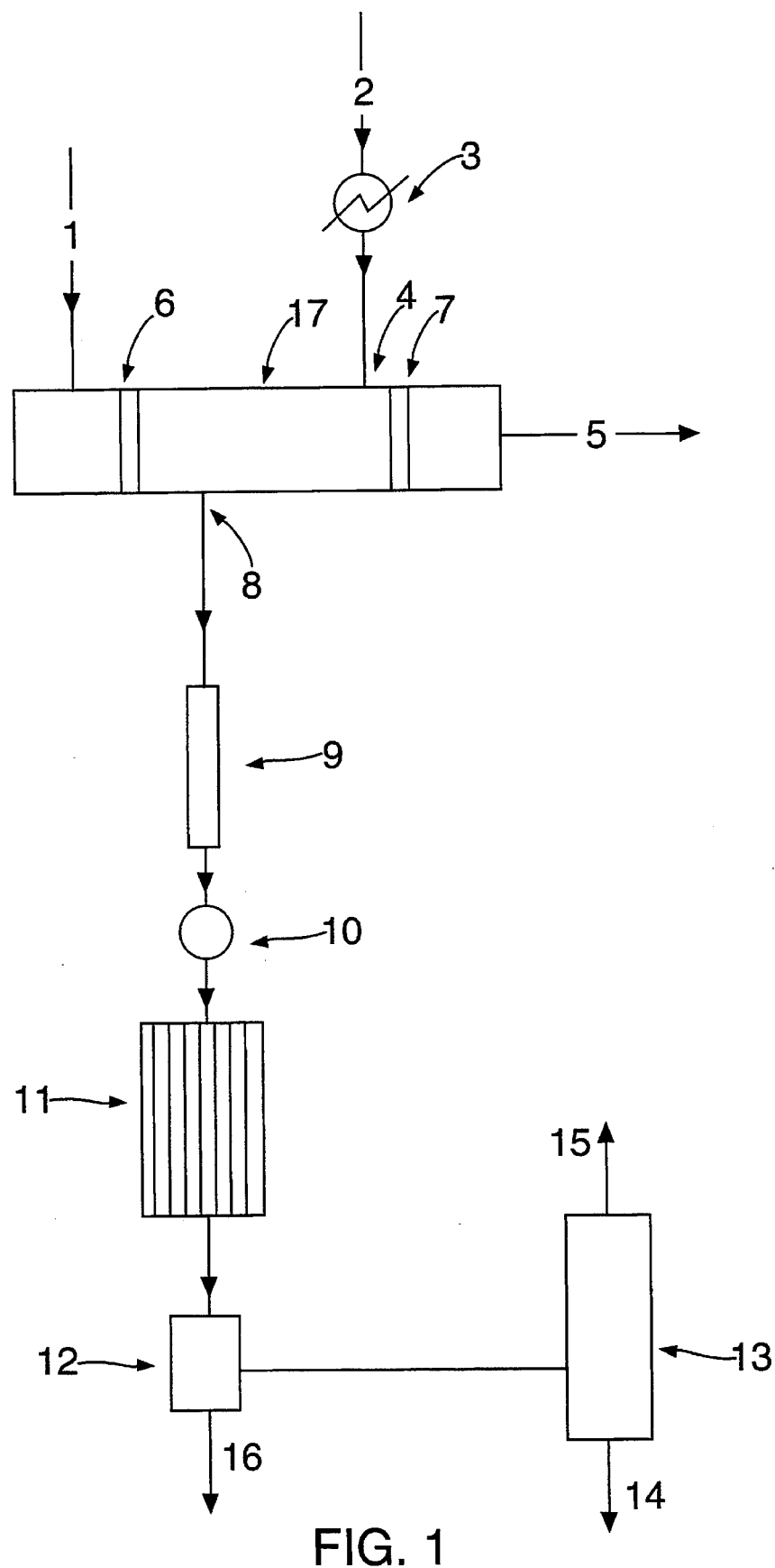
FIG. 1 is a schematic diagram of an embodiment of the invention.

As used herein, "multi-component, polymeric waste material" denotes material or articles that include at least one hydrolyzable polymeric component and at least one other component which may be a non-hydrolyzable polymer, an inorganic or organic material, or other types of materials, and that have been, is intended to be, or otherwise would have been discarded by a consumer, manufacturer, distributor, retailers installer and the like. The other components can constitute from about 5 to about 95, preferably about 20 to about 80 weight percent of the multi-component, polymeric waste material. "Multi-component, polymeric waste material" does not include scrap hydrolyzable polymeric and/or oligomeric material generated during the production of intermediate articles such as fiber, chip, film or molded articles which intermediate articles are then incorporated or transformed into end use multi-component products such as carpets and packaging. Examples of such scrap material are yarn waste, chip waste or extruder slag.

The hydrolyzable polymers with which this invention is particularly suitable include polyamide, especially nylon 6 and nylon 6,6, and polyester, especially polyethylene terephthalate. The recovered monomers are those from which the hydrolyzable polymer is formed. In the case of polyamide, the recovered monomers can be a dicarboxylic acid and an alkylene diamine or a lactam. With nylon 6 the recovered monomer is caprolactam and with nylon 66 the recovered monomers are adipic acid and hexamethylene diamine. In the case of polyester, the recovered monomers cash be a dicarboxylic acid and a dihydric alcohol. With polyethylene terephthalate the recovered monomers are terephthalic acid and glycol.

One useful embodiment is the recovery of monomer from waste carpet material that includes a hydrolyzable polymer as the face fiber. Particularly useful is the recovery of caprolactam from waste carpet material that includes nylon 6 face fiber and non-nylon 6 components.

As used herein, "fiber" denotes an elongate body, the length dimension of which is much greater than the transverse dimensions of width and thickness. Accordingly, "fiber" includes, for example, monofilament, multifilament yarn (continuous or staple), ribbon, strip, staple and other forms of chopped, cut or discontinuous fiber, and the like having regular or irregular cross-sections. "Fiber" includes a plurality of any one of the above or a combination of the above.

As used herein, "carpet material" denotes carpet which has not been subjected to any mechanical separation (referred to herein as "whole carpet") and any mixture of carpet components that is a product of separation, mechanical or otherwise, of whole carpet (referred to herein as "beneficiated carpet"). "Waste carpet material" denotes carpet material that has been, is intended to be, or otherwise would have been discarded by a consumer, manufacturer, distributor, retailer, installer and the like.

An important advantage of the invention with respect to carpet is that it eliminates the need for mechanical separation of the nylon 6 face fiber from the backing material and adhesive. The process of the invention utilizes chemical mechanisms to separate these components. In fact, carpet without any prior treatment, including uncleansed waste carpet, may be used as the feedstock. Cleaning is not necessarily required because most of the dirt would not be present in the aqueous solution formed during the process of the invention and, thus, would be removed when the aqueous solution is separated from the water insoluble portion. In addition, removal of any treatment agents that have been applied to the face fiber such as stainblockers, soil repellants or stabilizers also is not required. The carpet, however, may be mechanically reduced to strips or pieces of appropriate size to facilitate handling. Another advantage of the process is that it is sufficiently flexible so that it may use as a feedstock beneficiated carpet that includes nylon 6 face fiber that has been separated by mechanical means from part or most of the backing material and adhesive, if desired.

In the first stage of the process the multi-component material feedstock that includes a hydrolyzable polymeric component is combined with liquid water in an enclosed space and heated at a sufficient temperature for a sufficient length of time to effect an initial hydrolytic depolymerization of the hydrolyzable polymeric component and dissolve the resulting depolymerization products into the water without dissolving a substantial amount of the other components of the material. This first stage is also referred to herein as a "prehydrolysis" step.

The first stage can be carried out in a high pressure reactor operated batchwise or continuously. The particular type of reactor used is not critical to the process. An autoclave, optionally equipped with means for mechanical agitation, may be used for batch or continuous operation. In a batch operation the multi-component material may be charged to the reactor at atmospheric pressure and then superheated steam added under pressure to raise the temperature and pressure to the desired levels. Alternatively, both the multi-component material and water may be charged under atmospheric pressure and the vessel heated externally. A combination of steam and water may also be used to achieve the desired temperature. In a continuous operation an extruder may be used to feed the carpet feedstock to the reactor. In one embodiment of this invention an extruder may be used both as the feeder and the reactor for the first stage. Such an extruder will have ports for introducing the multi-component material and water and appropriate seals so that the water remains in the liquid phase for a substantial portion of the residence time in the extruder.

The amount of water used relative to the multi-component material should be sufficient to dissolve a substantial portion of the hydrolyzable polymeric component and depolymerization products and extract them from the other components present in the multi-component material. The amount of water may be reduced by using several reactors in series for this stage, and feeding the water countercurrently to the flow of the water insoluble stream. The greatest economy in water consumption is achieved by using an extruder to effect a continuous countercurrent operation, as will be described further below. The amount of water used relative to the amount of hydrolyzable polymer in the multi-component material will depend on the desired hydrolyzable polymer and depolymerization product recovery, the hydrolyzable polymer content of the carpet, the temperature, and the mode of extraction. The higher the desired recovery, the higher the required amount of water. The higher the temperature of the reaction, the lower the amount of water.

The water may be supplied as liquid water, superheated steam or as a mixture of liquid water and steam. In the last two instances a compressor may be used to obtain the desired temperature and pressure. In any case, the steam entering the reactor condenses into liquid water because the reactor pressure is at least equal to the vapor pressure of water. Due to the presence of the liquid water the liquid aqueous solution is able to form during the first stage.

The reaction temperature during the first stage should be greater than the melting point of the hydrolyzable polymeric component. Preferably, the temperature should be at least about 5, more preferably at least about 10° C. above the melting point.

The second stage of the process of the invention is separation of the liquid aqueous phase and the water insoluble phase formed by the first stage. The separation can occur at substantially the same temperature and pressure that exists in the first stage, although the temperature and pressure may be lowered somewhat to facilitate separation. Substantial reduction of temperature, however, is not preferred because it is wasteful of energy. The physical state of the insoluble components at this point in the process depends upon the composition of the multi-component material feedstock used in the first stage and on the temperature of the second stage. The insoluble components may be solid or may have melted, either partially or completely, and they may have mixed or reacted together.

The third stage of the process involves a flashing step. "Flashing" is a well known separation operation involving quickly vaporizing a portion of a liquid in such a way that the evolved vapor is in equilibrium with the residual liquid (see, e.g., McCabe and Smith, Unit Operations of Chemical Engineering, pp. 533–34 (McGraw-Hill 1976)). Preferably, the third stage of the process contemplates introducing the aqueous solution into a high temperature reactor maintained at a lower pressure relative to that of the first two stages in order to continue the depolymerization and form additional monomer, which is separated. Viewed another way, the pressure maintained during the first two stages is released adiabatically from a closed system in the third stage. The pressure during the third stage should range from subatmospheric, i.e., about 10 kPa, to about 1400 kPa. The flashing causes instant cooling but the temperature in the third stage is increased to a high level by heat input through the walls of the reactor or via injection of superheated steam.

The process of the invention is described below in more detail using carpet waste material having nylon 6 face fiber as an example of waste material.

The first or prehydrolysis stage of the process is an extraction or leaching step during which there are formed two fractions: (1) a liquid aqueous solution which includes a majority amount of, if not substantially all, the initial nylon 6 depolymerization products and (2) a water insoluble portion which includes a majority amount of, if not substantially all, the non-nylon 6 components. The nylon 6 depolymerization products formed during this stage may be collectively called "nylon 6 hydrolyzate" and include nylon 6 of reduced molecular weight, caprolactam, and both the linear and cyclic oligomers of caprolactam.

At least about 60, preferably at least about 80, and most preferably at least about 90, weight % of the nylon 6 depolymerization products formed during the first stage, based on the weight of the amount of nylon 6 depolymerization products theoretically available in the carpet feedstock, should be dissolved in the aqueous solution formed in the first stage. Viewed another way, the first stage extracts about 60, preferably at least about 80, and most preferably at least about 90, weight % of the nylon 6 of the nylon 6 theoretically available in the carpet feedstock. The nylon 6 depolymerization products form the major constituent of the liquid aqueous solution. By "major constituent" it is meant that the mixture of nylon 6 depolymerization products is the largest constituent or component of the liquid aqueous solution by weight, excluding water. Preferably, the resulting concentration of nylon 6 depolymerization products in the liquid aqueous solution should be at least about 5, more preferably at least about 15, and most preferably at least about 25, weight %. Typically, the maximum concentration of nylon 6 depolymerization products in the liquid aqueous solution can reach up to about 50 weight %, preferably up to about 75 weight %.

The water insoluble portion resulting from the first stage should include at least about 90, preferably about 95, and most preferably about 99, weight % of the non-nylon 6 components, based on the weight of the non-nylon 6 components in the carpet feedstock. In particular, if the waste carpet material includes calcium carbonate, polypropylene and SBR latex, the water insoluble portion should include about 99.8 to about 96.5 weight % of the calcium, and about 90 to about 99 weight % the non-nylon 6 components other than calcium carbonate. The non-nylon 6 components form the major constituent of the water insoluble portion. By "major constituent" it is meant that the mixture of non-nylon 6 components is the largest constituent or component of the water insoluble portion by weight, excluding absorbed or entrained water. Preferably, the resulting amount of non-nylon 6 components in the water insoluble portion should be at least 90, more preferably at least 95, weight %, based on the weight of the water insoluble portion exclusive of absorbed or entrained water. Typically, the maximum amount of non-nylon 6 components in the water insoluble portion can reach up to about 99 weight %, based on the weight of the water insoluble portion exclusive of absorbed or entrained water.

It is evident that it is important that the reaction mixture in the first stage include a liquid aqueous phase into which the depolymerization products can dissolve. Small amounts of nylon 6 depolymerization products, however, are lost in the water insoluble portion by virtue of reduced solubility in the aqueous solution, increased solubility, absorption, adsorption, or mechanical entrainment in the water insoluble phase, or other physical effects. Generally, the higher molecular weight fraction of said products tends to remain in the water insoluble portion. The loss can be minimized by operating at higher temperatures, using larger amounts of water, and increasing the contact time between the carpet material and water.

The preferred amount of water is about 0.5 to about 5, especially about 1 to about 2, parts of water per part nylon 6 present in the carpet.

The reaction temperature during the first stage should be at least about 240° C. At lower temperatures reaction of nylon 6 with water is very slow. Higher temperatures increase the rate of reaction and minimize the amount of nylon 6 depolymerization products that remain in the water insoluble phase, but also require higher pressure because of the increased vapor pressure of water. A temperature range of about 240° to about 370° C. is appropriate for the first stage, with a preferred range of about 250° to about 350° C. The pressure during the first stage should be at least equal to the vapor pressure of water, which is dependent, of course, upon the water temperature.

The contact time between water and the carpet material will depend mainly on the temperature and the amount of water used. Generally, the higher the temperature and the greater the amount of water, the lower the required contact time required. Contact times should range from about 1 minute at 350° C. to about 1 hour at 250° C. The short contact times combined with the higher temperatures are preferred if this stage is carried out in an extruder. "Contact time" as used herein is the time during which water is intimately mixed with the carpet material. In a batch reactor it is equal to the time elapsed from the moment that the mixture of water and carpet has reached the desired temperature and pressure to the moment that the mixture is discharged from the reactor. In a continuous flow isothermal stirred reactor it is equal to the residence time in the reactor. In an extruder it is equal to the residence time in the extruder mixing zone.

The first stage accomplishes two tasks: the dissolution of nylon 6 in water and the partial depolymerization of nylon 6. The nylon 6 dissolution and the nylon 6 depolymerization may occur simultaneously. Depolymerization is manifested by an increase in the concentration of amine and carboxylic end groups and by formation of caprolactam. To the extent that caprolactam is formed in this stage, it is not adversely effected by the subsequent stages of the process and remains available to constitute a portion of the desired product. Although not wishing to be bound by any theory, it is surmised that the simultaneously occurring depolymerization and dissolution phenomena have a synergistic effect upon each other. The caprolactam being produced during the first stage appears to facilitate the dissolution of additional nylon 6 and its oligomers. Furthermore, it is believed that the high concentration of end groups contributes to the continuance of depolymerization in the subsequent stages of the process. Moreover, as the degree of depolymerization increases the solubility of the nylon 6 hydrolyzate in water increases and the viscosity of the liquid aqueous solution decreases. Because of the decreased viscosity, the liquid aqueous solution and the water insoluble portion tend to achieve a more distinct separation.

Separation of the liquid aqueous solution that includes the nylon 6 depolymerization products and the water insoluble portion can be performed via any conventional means and can occur at substantially the same temperature and pressure that exists in the first stage. If whole carpet is used as the feedstock, the insoluble matter after the first stage is a rubbery mass that is easily separable by filtration or decanting from the aqueous phase. If most of the latex has been removed prior to the first stage, the insoluble residue is chiefly polypropylene, which may be a viscous liquid or a solid depending on the temperature. If the insoluble components are in the form of a liquid, they are conveniently separated by decanting; if they are in a form of a solid, by filtration or decanting. The separation is performed to remove as much of the aqueous phase as practical. Filtration of the solids may be followed by blowing an inert gas such as nitrogen through the filter cake and the adhering liquor further removed by washing the cake with hot water. Wash liquors may be recycled into the first stage of the process.

At the conclusion of the second stage, the liquid aqueous portion should include about 5 to about 75, preferably about 5 to about 50, more preferably about 15 to about 50, weight % nylon 6 depolymerization products and less than about 10, preferably less than about 2, weight % of non-nylon 6 components that solubilized or were not separated. About 10 to about 80 weight % of the nylon 6 depolymerization products is caprolactam. The insoluble portion includes non-nylon 6 components such as polypropylene, polypropylene degradation products, latex, latex degradation products, fillers, fiber additives and treatment materials, and any nylon 6 and nylon 6 depolymerization products that were not extracted from the reaction mixture. The amount of nylon 6 recovered after the second stage (i.e., the total amount of nylon 6 depolymerization products present in the aqueous portion) compared to the amount of nylon 6 in the carpet feedstock is dependent upon the amount of water used, the temperature, the mode of extraction (single or multiple stage, co-current or countercurrent) and the extent that the carpet feedstock has been enriched by prior separation of the components. Substantially complete recovery of the nylon 6 is possible, but the economically practical recovery should be about 90 to 98 weight %, preferably at least about 95 weight %, based on the weight of the nylon 6 in the carpet feedstock.

In one embodiment the first and second stages of the process may both be carried out in an extruder equipped with means for concurrent or countercurrent contact of a liquid with a plastic and separate outlets for the liquid and plastic phases. Such an extruder is described in U.S. Pat. No. 3,742,093 to Skidmore. Countercurrent flow is preferred because it accomplishes a more thorough removal of nylon 6 from the non-nylon 6 components of the carpet with the minimum amount of water. The water is supplied under pressure and is preferably preheated. Alternatively, steam or a mixture of water and steam may be provided and a compressor used to produce hot water. The temperature of the mixture in the extruder is preferably about 280° to about 370° C.

The third stage of the process of the invention involves introducing the aqueous solution into a high temperature reactor maintained at a lower pressure relative to that of the first two stages in order to continue the depolymerization and form additional caprolactam. The caprolactam formed during the first stage that is present in the aqueous portion at the beginning of the third stage and the caprolactam formed during the third stage is separated via distillation. The distillate is a mixture of water and caprolactam. The residue includes any non-nylon 6 components that were not separated during the preceeding stages and nylon 6 depolymerization products other than caprolactam.

Specifically, a substantially large portion of water and caprolactam present in the aqueous portion flash off immediately at the beginning of the third phase. The gaseous water and caprolactam mixture is collected. During the third stage, additional caprolactam is formed by depolymerization and it likewise is distilled from the mixture.

The caprolactam may be recovered from the gaseous distillate via conventional techniques. For example, the gaseous distillate may be condensed and water evaporated to leave a crude caprolactam residue. Alternatively, the gaseous distillate may be subjected to partial condensation to provide a condensate containing about 50 to about 95 weight % caprolactam and the overheads (consisting substantially of water vapor) may be recycled to the first stage. Crude caprolactam may then be recovered by eliminating water from the condensate via evaporation. Caprolactam of polymerization grade may be obtained by further purification via known chemical treatment, distillation and/or crystallization techniques.

A conventional depolymerization catalyst such as phosphoric acid may be added in the third stage. A catalyst, however, is not preferred because the rate of depolymerization during the third stage is adequate due to the initial depolymerization effected in the first stage of the process. Moreover, any alkali materials that still remain in the mixture at the third stage may react with the acidic catalyst.

The high temperature reactor of the third stage may be a tank in which superheated steam is injected through the liquid mass or it may be a pipe or a bundle of pipes heated externally, e.g., electrically or by contact with hot combustion gases. Mechanical agitation may be also used to improve heat transfer. For example, a wiped film evaporator may be used as the reactor for the third stage. The temperature is maintained between about 270° and 400° C., preferably between about 290° and 350° C.

The pressure in this stage depends on the temperature used. At a lower temperature range of about 270° to 300° C. the pressure should be close to atmospheric. Sub-atmospheric pressures, e.g. down to about 10 kPa, may also be used but they offer no particular advantage and are not preferred. At higher temperatures of about 300° to 350° it is advantageous to operate at somewhat elevated pressures, e.g., up to about 1400 kPa at 350° C. A beneficial effect of increasing the pressure in this stage is the suppression of the amount of cyclic oligomers that distill with caprolactam. Such oligomers are formed during depolymerization along with caprolactam. Elevated pressure also results in a high depolymerization rate. Excessive pressures, however, have a detrimental effect because distillation of caprolactam is hindered.

In the third stage, it is possible to recover substantially all the caprolactam that is theoretically available from the nylon 6 depolymerization products recovered in the first two stages. If such a complete recovery is sought, however, the amount of impurities in the crude caprolactam product of the depolymerization reaction is increased. It is presumed that this is due to two causes. First, non-nylon 6 impurities present in the aqueous solution increase in concentration as caprolactam is removed. The higher the concentration of these impurities the higher the rate at which they decompose to volatile by-products that contaminate the caprolactam product. Second, depolymerization of the low molecular weight nylon 6 is accompanied by concurrent condensation reactions that elevate the molecular weight and decrease the rate of reaction. Consequently, caprolactam production slows down as conversion increases. This may be compensated for by increasing the temperature or introducing a catalyst. These expedients, however, generally increase the amount of by-products formed. Increased temperature also results in increased amounts of cyclic oligomers distilling with caprolactam. It is preferred, therefore, to limit the caprolactam recovery to about 50 to 95 weight %, preferably to about 70 to 95 weight %, of the amount of caprolactam theoretically recoverable from the nylon 6 depolymerization products recovered in the first two stages.

The purity of the distillate from the third stage (i.e., the mixture of caprolactam and water) after the water has been evaporated should range from about 96 to 99 weight % caprolactam, based upon the total weight of the dried distillate. The 1 to 4 weight % of impurities in the dried distillate are for the most part low molecular weight cyclic oligomers of caprolactam. If beneficiated carpet is used as the feedstock, the purity will tend to be higher. If there is a significant amount of dirt on the carpet, the purity will tend to be lower.

Residuals non-distilled material can be recycled to the first stage, where high molecular weight nylon 6 formed in the third stage is depolymerized to lower weight material and caprolactam. Cyclic oligomers that have accumulated in the residue are also hydrolyzed in the first stage. Non-nylon 6 impurities that have accumulated in the residue of the third stage can be rejected by the phase separation of the second stage.

Optionally, the aqueous solution from the second stage may be held at an elevated temperature and pressure to further advance depolymerization prior to the third stage. This is particularly pertinent when an extruder is used to perform the first two stages. Because of the high capital cost of the extruder, it is desirable to obtain the highest throughput coupled with the highest extraction of nylon 6 by water in the extruder. A degree of depolymerization that is sufficient to effect high extraction is not necessarily optimal for subsequent recovery of caprolactam in the third stage. Holding the aqueous phase for an additional time at the high temperature and pressure available at the extruder exit can be accomplished inexpensively by letting the aqueous solution flow though a tube or baffled vessel of appropriate dimensions prior to releasing the pressure into the third stage. The residence time will be a few minutes.

FIG. 1 is a schematic diagram of a preferred embodiment of the process of the invention. A carpet with face fiber of nylon 6 and backing of polypropylene and calcium carbonate-filled SBR latex is chopped to small pieces and continuously fed at 1 to a twin screw extruder 17 equipped with appropriate water tight seals 6 and 7, inlets and outlets for countercurrent contact with a fluid. Water 2 is pumped under pressure through a heater 3 that raises its temperature to over 300° C. It enters the extruder at 4 and flows countercurrent to the flow of the extrudate which exits at 5. The extrudate is substantially free of nylon 6. The temperature in the space between 6 and 7 is maintained at 300° to 350° C. The pressure is sufficiently high to substantially maintain water in the liquid phase. The hot water feed and the mechanical energy of extrusion supply most of the heat required. External electric heating is supplied as required to maintain the temperature. The aqueous phase exits at 8 to a tube 9 held at substantially the same temperature and pressure as the extruder. It is discharged through a pressure reducing valve 10 into a bundle of vertical tubes 11 held at a reduced pressure relative to that in the extruder. The reduced pressure can range from atmospheric to 1400 kPa. The temperature in the interior of the tubes is maintained at 300° to 350° C. by means of external heating. The mixture from 11 flows into distillation unit 12 from which residue 16 is collected and vapor is directed to a partial condenser 13. At partial condenser 13 crude caprolactam 14 containing a small amount of water is condensed. Steam 15 that flows overhead may be utilized to preheat fresh water used at 2 or fed directly at 2 through a compressor. The residue 16 is recycled to the extruder along with the carpet. A portion of the residue may be purged as a bleed stream to forestall accumulation of impurities that do not exit with the extrudate at 5.

The following examples are presented to demonstrate the advantages of the invention. The specific techniques, conditions, materials, proportions and reported data set forth to illustrate the principles of the invention are exemplary and should not be construed as limiting the scope of the invention. Unless otherwise stated, all parts and percentages are by weight.

EXAMPLE 1

One part of nylon 6 having a molecular weight of about 20,000 and 0.47 parts of water were placed in a stainless steel reactor, the reactor was sealed and then heated to 290° C. for 10 min. The molecular weight of the mixture (excluding caprolactam) at that point was about 1,000 and the amount of caprolactam present was about 20% of the total amount of caprolactam theoretically recoverable from the amount of nylon 6 charged to the reactor. The reactor was depressurized to 650 kPa and superheated steam was sparged through the bottom at the rate of 0.4 parts per minute. The temperature of the liquid was brought rapidly to 330° C. with the aid of externally applied heat and maintained at that temperature for the duration of the run. Distillate cuts were collected every 20 minutes and analyzed for caprolactam. The caprolactam produced from the time the temperature reached 330° C. is plotted in FIG. 2, curve A as percent of the total amount theoretically recoverable based on the amount of nylon 6 charged. The time line plotted as the abscissa begins when the temperature reaches 330° C. After 225 minutes the run was stopped. The reactor contained 0.03 parts of residue that was essentially free of water.

The run was repeated under the same conditions, except that the prehydrolysis of nylon 6 was omitted. That is to say, no water was placed in the reactor prior to heating and there was no heating to 290° C. for 10 min. Instead, a sealed reactor containing nylon 6 only was rapidly heated to 330° C. with the aid of externally applied heat and maintained at that temperature for the duration of the run. As in the other run, steam was sparged through the bottom at the rate of 0.4 parts per minute at 650 kPa once the temperature reached 330° C. The caprolactam produced from the time the temperature reached 330° C. is plotted in FIG. 2, curve B. After 225 minutes the run was stopped.

Figure 2:
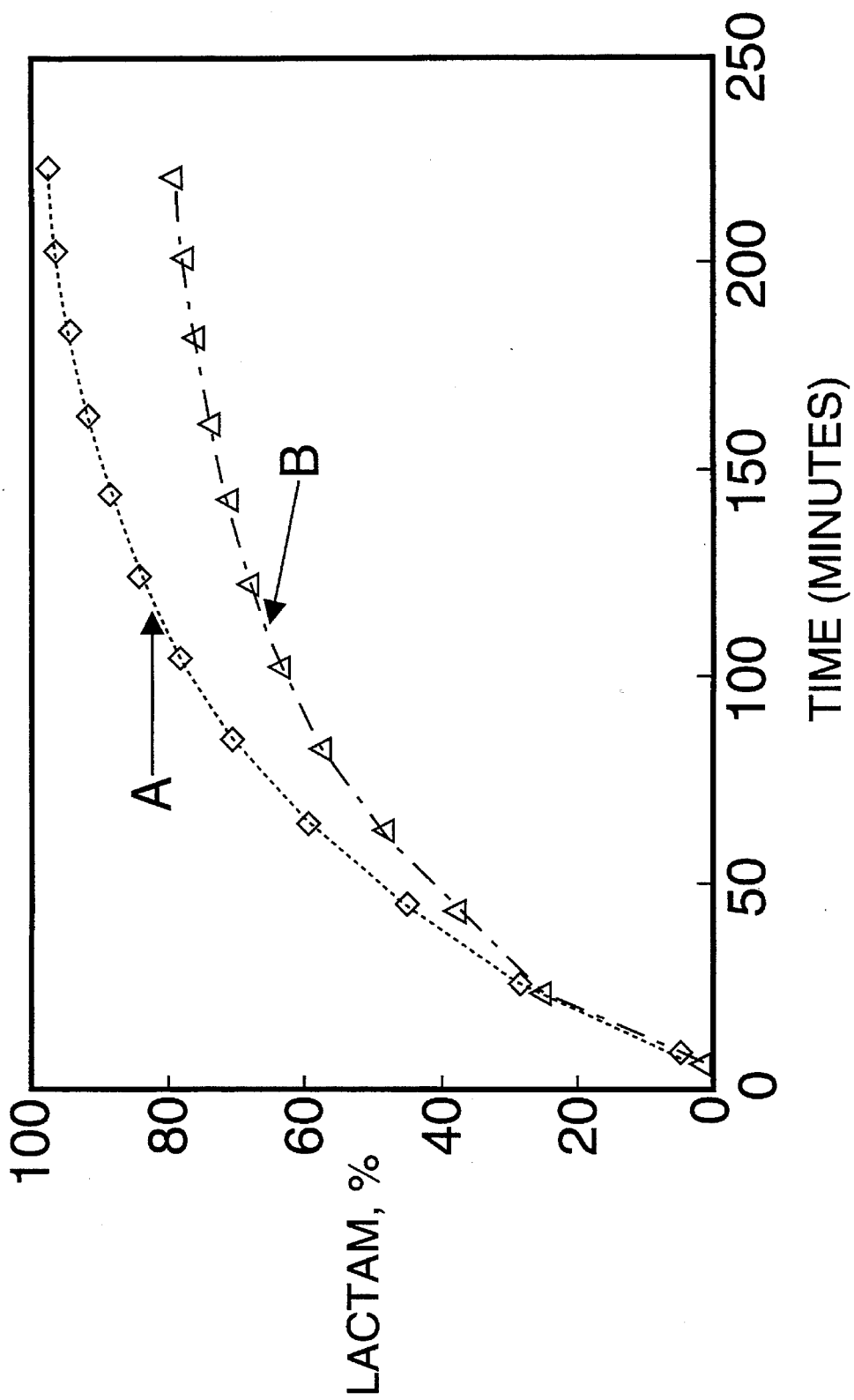
FIG. 2 is a graph illustrating one advantage of the invention.

It is evident from FIG. 2 that the rate of caprolactam formation was lower in the absence of prehydrolysis. The prehydrolysis performed in this example is analogous to the partial depolymerization occurring in the first stage of the invention. The reaction of the steam and the nylon 6 is analogous to the depolymerization occurring in the third stage of the invention. The results of this example indicate that the partial depolymerization in the first stage improves the rate of depolymerization occurring in the third stage.

EXAMPLE 2

A carpet having nylon 6 face fiber and backing of polypropylene and calcium carbonate-filled SBR latex contained 34.9% nylon 6 and 32.6% calcium carbonate. One part of the carpet, cut to small pieces, and 1.51 parts of water were placed in an autoclave, the autoclave was sealed and then heated to 290° C. for 30 minutes. The temperature was reduced to 90° C., the autoclave was opened and the liquid was separated from the solids via filtration at atmosphere pressure. Analysis of the filtrate showed that 73% of the nylon 6 charged had been extracted. Washing the solids twice with 1.51 parts of water each time brought the amount of nylon 6 extracted to 97% of nylon 6 charged. Less than 0.7% of the calcium present in the carpet was extracted.

EXAMPLE 3

A carpet having nylon 6 face fiber and a backing of polypropylene and calcium carbonate-filled SBR latex contained 34.9 wt. % nylon 6 and 32.4 wt. % calcium carbonate. One part of the carpet, cut into small pieces, and 1.5 parts of water were placed in an autoclave, sealed and heated to 290° C. for 30 minutes. The autoclave was cooled to 220° C. and the liquid discharged through a filter under pressure. Analysis of the filtrate showed that 86 wt. % of the feedstock nylon 6 has been extracted as a mixture of caprolactam and nylon 6 oligomers. The filtrate also contained 2.4 wt. % of calcium in the feedstock.

COMPARATIVE EXAMPLE 4

The procedure of Example 3 was repeated, except that the mixture in the autoclave was heated at 230° C. for 30 minutes. The filtrate contained 31 wt. % of the nylon 6 in the feedstock and 0.35 wt. % of the calcium in the feedstock. This example demonstrates that at a temperature close to the melting point of nylon 6 the recovery of nylon 6 depolymerization products during the prehydrolysis step is substantially inferior compared to a temperature above the melting point.

EXAMPLE 5

One hundred parts of the carpet of Example 2 and 150 parts of water were charged to an autoclave, the autoclave was sealed and heated for 30 minutes at 290° C. The autoclave was cooled to 160° C. and the liquid was discharged continuously through a filter and a valve at the rate of 1.2–1.4 parts per minute into the top opening of a vertical ¼ inch diameter, 12 inch long stainless steel tube held at 330° C. and at atmospheric pressure. Vapors exited from a side arm at the bottom of the tube and were condensed in a water cooled condenser. The non-volatilized material collected in a receiver at the bottom of the tube. The estimated residence time of the vapors in the tube was 0.5 seconds. After 105 minutes, 163 parts of condensate was collected containing 15% caprolactam, which corresponds to a recovery of 70% of the nylon 6 charged. A second extraction of the material remaining in the autoclave with 150 parts of water followed by depolymerization in the vertical tube resulted in an additional condensate recovery of caprolactam corresponding to 15% of the charged nylon 6, bringing the total recovery to 85% of the charged nylon 6. After evaporation of water from the condensate collected from the depolymerization tube, the caprolactam was 97% pure by High Performance Liquid Chromatography (HPLC) analysis. The main impurity was 1.4% of caprolactam cyclic dimer. 8.6 parts of a solid non-volatized material was also collected in the receiver at the bottom of the tube. This consisted of 86% nylon 6 of molecular weight of about 20,000 in mixture with non-nylon 6 components.

From the foregoing description, one skilled in the art can easily ascertain the essential characteristics of this invention, and without departing from the spirit and scope therof, can make various changes and modifications of the invention to adapt it to various usages and conditions.

We claim:

1. A process for recovering monomer from a multi-component polymeric waste material that includes at least one hydrolyzable polymeric component, comprising:

(a) subjecting a mixture of water and the multi-component polymeric waste material to heat and pressure to form a liquid aqueous solution which includes as a major constituent a mixture of depolymerization products of the hydrolyzable polymeric component and a water insoluble portion which includes as a major constituent a mixture of materials other than the depolymerization products;

(b) separating the liquid aqueous solution and the insoluble portion;

(c) flashing and heating the liquid aqueous solution to produce a distillate which contains at least one type of monomer that formed the hydrolyzable polymeric component and a residue; and (d) separating the monomer in the distillate from other components in the distillate.

2. A process according to claim 1, wherein step (a) comprises subjecting the waste material/water mixture to a pressure at least equal to the vapor pressure of water.

3. A process according to claim 1, wherein step (a) comprises subjecting the waste material/water mixture to a temperature that is at least about 10° C. above the melting point of the hydrolyzable polymeric component.

4. A process according to claim 1, wherein step (c) comprises subjecting the liquid aqueous solution to a pressure of about 10 kPa to about 1400 kPa.

5. A process according to claim 1, wherein the hydrolyzable polymeric component is selected from the group consisting of nylon 6, nylon 66 and polyethylene terephthalate.

6. A process according to claim 1, wherein the hydrolyzable polymeric component comprises a polyamide and the monomer comprises a lactam.

7. A process according to claim 1, wherein the hydrolyzable polymeric component comprises a polyamide and the monomer comprises at least one of the group consisting of a dicarboxylic acid and an alkylene diamine.

8. A process according to claim 1, wherein the hydrolyzable polymeric component comprises a polyester and the monomer comprises at least one of the group consisting of a dicarboxylic acid and a dihydric alcohol.

9. A process for recovering caprolactam from carpet material that includes nylon 6 and non-nylon 6 components, comprising:

(a) subjecting a mixture of water and the carpet material to heat and pressure to form a liquid aqueous solution which includes as a major constituent a mixture of nylon 6 depolymerization products and a water insoluble portion which includes as a major constituent a mixture of non-nylon 6 components;

(b) separating the liquid aqueous portion and the water insoluble portion;

(c) subjecting the liquid aqueous portion to a pressure that is lower than that of step (a) and heat to produce a residue and a distillate which contains caprolactam; and (d) separating the caprolactam in the distillate from other components in the distillate.

10. A process according to claim 9, wherein step (a) comprises subjecting the carpet/water mixture to a temperature of about 240° to about 370° C. and a pressure at least equal to the vapor pressure of water.

11. A process according to claim 9, wherein the amount of water contacted with the carpet material is from about 0.5 to 5 parts of water per one part nylon 6 present in the carpet material, based on weight.

12. A process according to claim 9, wherein the carpet material is in the form of a stream and the water is in the form of a stream and the carpet material stream and the water stream are contacted countercurrently to effect extraction of the nylon 6 depolymerization products from the carpet material.

13. A process according to claim 9, wherein step (a) comprises subjecting the carpet/water mixture to sufficient heat and pressure to initiate depolymerization of nylon 6 and extract the resulting nylon 6 depolymerization products from the carpet material into the liquid aqueous portion.

14. A process according to claim 9, wherein step (b) comprises decanting, filtering, or a combination of decanting and filtering.

15. A process according to claim 9, wherein about 90 to 98 weight % of the nylon 6 present in the carpet material is included in the liquid aqueous portion after step (b).

16. A process according to claim 9, wherein step (c) is effected without a catalyst.

17. A process according to claim 9, further comprising recycling the residue from step (c) to mix with the carpet material feed in step (a).

18. A process according to claim 9, wherein the carpet material comprises a carpet having nylon 6 face fiber and a backing material that includes non-nylon 6 components.

19. A process according to claim 18, wherein the non-nylon 6 components include at least one material selected from the group consisting of jute, polypropylene, latex, calcium carbonate, clay and hydrated alumina.

20. A process according to claim 9, wherein the liquid aqueous solution of step (a) includes about 5 to about 75 weight % nylon 6 depolymerization products, based on the total weight of the liquid aqueous solution.

21. A process according to claim 9, wherein the water insoluble portion of step (a) includes about 90 to about 99 weight % non-nylon 6 components, based on the total weight of the water insoluble portion exclusive of absorbed or entrained water.

22. A process for recovering caprolactam from a carpet material that includes nylon 6 and non-nylon 6 components, comprising:
   (a) introducing the carpet material and water into a first reactor;
   (b) subjecting the resulting mixture to heat and pressure to form a liquid aqueous portion which includes as a major constituent a mixture of nylon 6 depolymerization products and a water insoluble portion which includes as a major constituent a mixture of non-nylon 6 components;
   (c) separating the liquid aqueous solution and the water insoluble portion;
   (d) introducing the liquid aqueous solution into a second reactor;
   (e) subjecting the liquid aqueous solution to heat and pressure sufficient to produce a residue and a distillate which contains caprolactam; and
   (f) separating the caprolactam from other components in the distillate produced in step (e).

23. A process according to claim 22, wherein the carpet material is in the form of a stream and the water is in the form of a stream and the first reactor is an extruder, and step (b) comprises contacting countercurrently the carpet material stream and the water stream in the extruder while being subjected to a temperature of about 280° to about 370° C. and a pressure at least equal to the vapor pressure of water.

24. A process according to claim 22, wherein step (c) is performed in the extruder.

* * * * *